(12) United States Patent
Lund et al.

(10) Patent No.: US 6,379,330 B1
(45) Date of Patent: Apr. 30, 2002

(54) CONTAINER FOR A HYPODERMIC SYRINGE

(75) Inventors: Carsten Lund, Vordingborg; Erik Torngaard Hansen, Hundested, both of (DK)

(73) Assignee: Leo Pharmaceutical Products, Ltd. A/S (DK)

( * ) Notice: Subject to any disclaimer, the term of this patent is extended or adjusted under 35 U.S.C. 154(b) by 0 days.

(21) Appl. No.: 09/554,776

(22) PCT Filed: Nov. 19, 1998

(86) PCT No.: PCT/DK98/00503

§ 371 Date: May 18, 2000

§ 102(e) Date: May 18, 2000

(87) PCT Pub. No.: WO99/14995

PCT Pub. Date: Mar. 25, 1999

(30) Foreign Application Priority Data

Nov. 20, 1997 (DK) .............................. 01329/97

(51) Int. Cl.[7] .......................... A61M 5/00; B65D 41/00
(52) U.S. Cl. .................................. 604/111; 215/253
(58) Field of Search ................................. 604/111, 192, 604/263, 198, 110, 164.08; 215/250, 251, 253; 220/265, 266, 268, 276

(56) References Cited

U.S. PATENT DOCUMENTS

| 3,008,570 | A | | 11/1961 | Roehr et al. .................. 206/43 |
| 3,934,722 | A | * | 1/1976 | Goldberg ..................... 205/365 |
| 4,402,418 | A | | 9/1983 | Ostrowsky ................... 215/252 |
| 4,479,586 | A | | 10/1984 | Csaszar ....................... 215/258 |
| 4,886,497 | A | | 12/1989 | Scholl, Jr. ................... 604/111 |
| 5,092,462 | A | * | 3/1992 | Sagstetter et al. ........... 206/366 |
| 5,098,404 | A | * | 3/1992 | Collins ........................ 604/199 |
| 5,372,590 | A | * | 12/1994 | Haber et al. ................. 604/192 |

FOREIGN PATENT DOCUMENTS

WO 94/20380 9/1994

* cited by examiner

*Primary Examiner*—Sharon Kennedy
(74) *Attorney, Agent, or Firm*—Ostrolenk, Faber, Gerb & Soffen, LLP

(57) ABSTRACT

A container (1) for a hypodermic syringe (3) and of the type which allows it to be seen or observed in another manner that the container has been opened. The container (1) comprises a plug (5) having more than one tamper-proof mechanism. This ensures both that the hypodermic syringe (3) can reach the user in a state which allows it to be seen whether it has been opened, and that, after use, it can be disposed of in such a state that re-use is impeded considerably.

8 Claims, 5 Drawing Sheets

CONTAINER FOR A HYPODERMIC SYRINGE

BACKGROUND OF THE INVENTION

The invention relates to a container for a hypodermic syringe of the type defined in the introductory portion of the main claim.

Hypodermic syringes are used both in medical environments (hospitals, health care centres, etc.) and in the field (at home, accidents, in the open, etc.) It is essential in both situations to ensure cleanliness and an indication as to whether the hypodermic syringe has been used before. This has manifested itself in a wish for several levels of safety mechanisms, also called tamper-proof or tamper-evident mechanisms. There is also a wish on the part of the users for simple disposal after use of the hypodermic syringe. This results in so-called waste management initiatives from the manufacturers.

Separate blister packaging of syringes and needles is known, where the parts must first be assembled, injection liquid must be taken from an ampoule, and the parts must be separated after use. Various types are available from e.g. Becton Dickinson, Sanosafe and Owen Mansfort. It is also known to use rigid packages.

SUMMARY OF THE INVENTION

Accordingly, the object of the invention is to provide a container for a hypodermic syringe which may be supplied to the user as an assembled whole, and which may be disposed of as an assembled whole by the user after use. Before use, the assembled whole comprises hypodermic syringe with needle, injection liquid, container, plug and closure. After use, the injection liquid has been injected and the hypodermic syringe is totally or partly empty and may have been rendered unusable. The needle need not be bent, broken or be made unusable in another possibly hazardous manner.

According to the invention, the container for a hypodermic syringe of the type which allows it to be seen or observed in another manner that the container has been opened, is characterized in that the container comprises a plug having more than one tamper-proof mechanism. This ensures that the container for a hypodermic syringe may be supplied to the user as an assembled whole and be disposed of as an assembled whole by the user after use, it being ensured that the container has not been opened before it is to be used, and that later attempts at use are rendered difficult.

According to the invention, the container for a hypodermic syringe may be characterized in that the plug includes both a full or divided film connection and a plurality of flaps, each of which constitutes a tamper-proof mechanism. At least two mutually independent mechanisms are obtained hereby.

It has been found particularly expedient in the container for a hypodermic syringe that the plug includes an annular film connection and two flaps.

According to the invention, the container for a hypodermic syringe may be supplied to the user with the hypodermic syringe with injection liquid and needle ready for use. This provides a disposable injection system which is easy to use and dispose of by the user.

Moreover, it has been found expedient that the plug is provided with a plurality of film hinges, a plurality of film connections, a plurality of projections and a plurality of knobs. It is hereby possible to form several different tamper-proof mechanisms.

When two film hinges are provided between the body of the plug and the lid formed by separation at the film connections by opening of the container, and projections are provided between the film hinges and are capable of being engaged with recesses in the body of the plug, and knobs are provided at the film hinges and engage the body of the plug only when the projections are in engagement with the recesses, a particularly expedient embodiment of the container according to the invention is achieved.

BRIEF DESCRIPTION OF THE DRAWINGS

The invention will be explained below with reference to the drawing, in which.

DETAILED DESCRIPTION OF THE PREFERRED EMBODIMENTS

Figure 1:
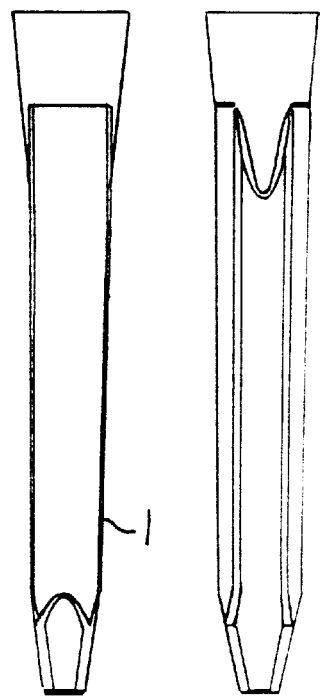
FIG. 1 shows a container seen in a three-rectangular view.

FIG. 1 shows the container 1 in which a hypodermic syringe generally designated by 3 (see FIG. 2) may be arranged. The container 1 is shown in FIG. 1 in a three-rectangular view. The container 1 is made as an injection-molded article of polypropylene. By suitable selection of parameters, polypropylene may form articles which are almost transparent, thereby allowing it to be seen whether there is something in the hypodermic syringe 3, and an optional label or print on the hypodermic syringe 3. The container shown in FIG. 1 is edged so as to be a tight fit in the package 7 (see FIG. 6).

Figure 2:
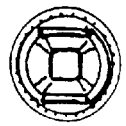
FIG. 2 shows the container with plug and hypodermic syringe seen in perspective, said parts being pulled apart.
Figure 2:
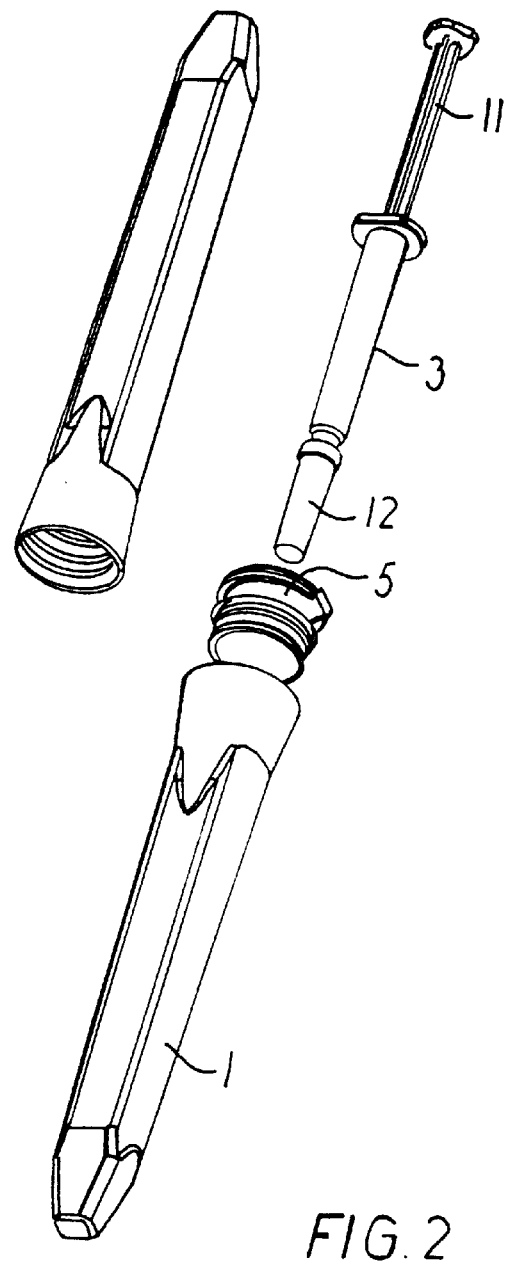

FIG. 2 shows the container 1, the hypodermic syringe 3 and the plug 5 which is used for closing the container 1. When the hypodermic syringe 3 is packed, the injection liquid is filled in a known manner into the hypodermic syringe 3, a piston 11 is inserted, and a needle (not shown) is covered by a needle case 12. The hypodermic syringe 3 is then placed in the container 1, and the plug 5 is applied.

Figure 3:
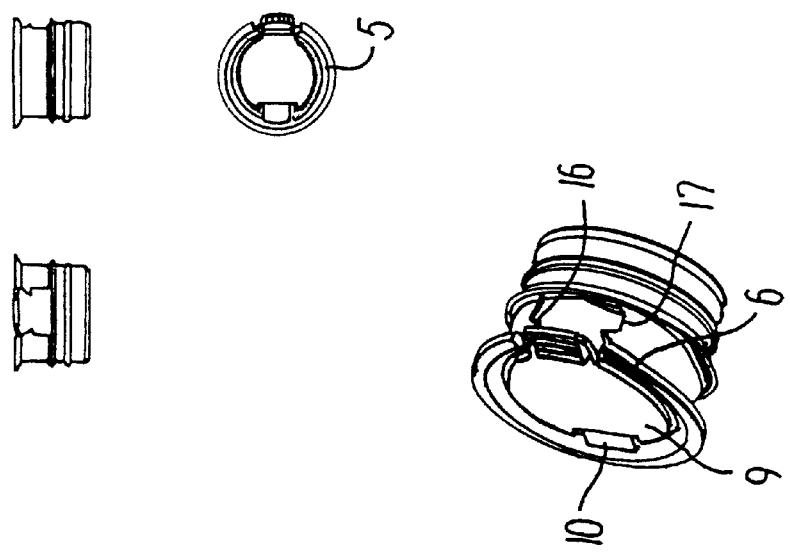
FIG. 3 shows the plug in detail in a three-rectangular view and in perspective.

FIG. 3 shows the plug 5 both in a three-rectangular view and in perspective. The plug 5 is injection-molded of polyethylene, which, by suitable selection of parameters and colour, may be provide properties that enable pilfer-proof, tamper-proof and tamper-evident properties. There is thus a film connection at 6, which may be injection-molded such that it may be broken without difficulty, and when it has been broken, it is easy to see that the container 1 has been opened. After use of the hypodermic syringe 3, it is moved down through the plug 5 into the container 1. The lid 9, which is formed by opening the plug 5 along the film connection 6, and which may tilt long the hinge 10, is then pressed so far down into the lug 5 that the flaps 16 and 17 hold the lid 9 in a position which does not readily allow re-opening of the container 1.

Figure 4:
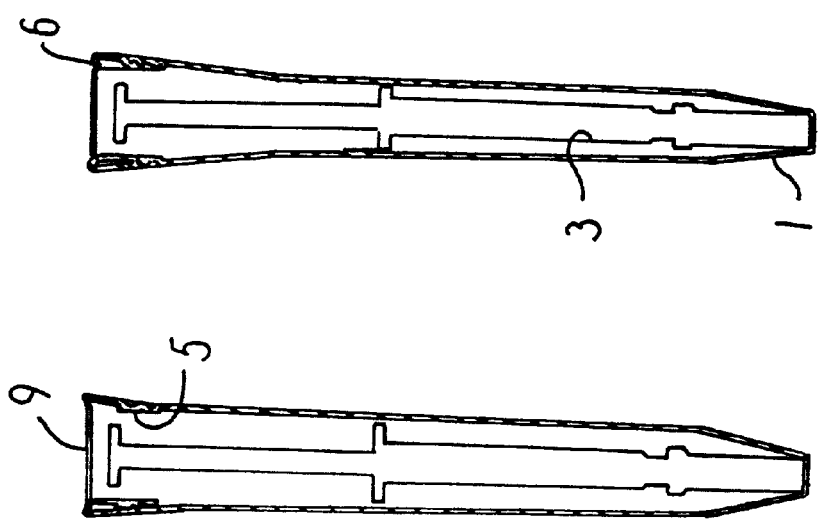
FIG. 4 shows the container and the hypodermic syringe seen in section in two mutually perpendicular and centrally positioned planes.

FIG. 4 is a sectional view of the hypodermic syringe 3 in the container 1. The hypodermic syringe 3 is unused, and the lid 9 is not removed from the plug 5 by rupture along the film connection 6. The needle case 12 is positioned over the needle (not shown). After opening of the container 1 the needle case 12 may be put back into the container 1, since the piston, after use, is pressed completely or partly down, thereby making room in the container 1 so that the needle need not be positioned in the needle case 12. This reduces the risk of e.g. the user getting unintentionally pricked by the needle.

Figure 5:
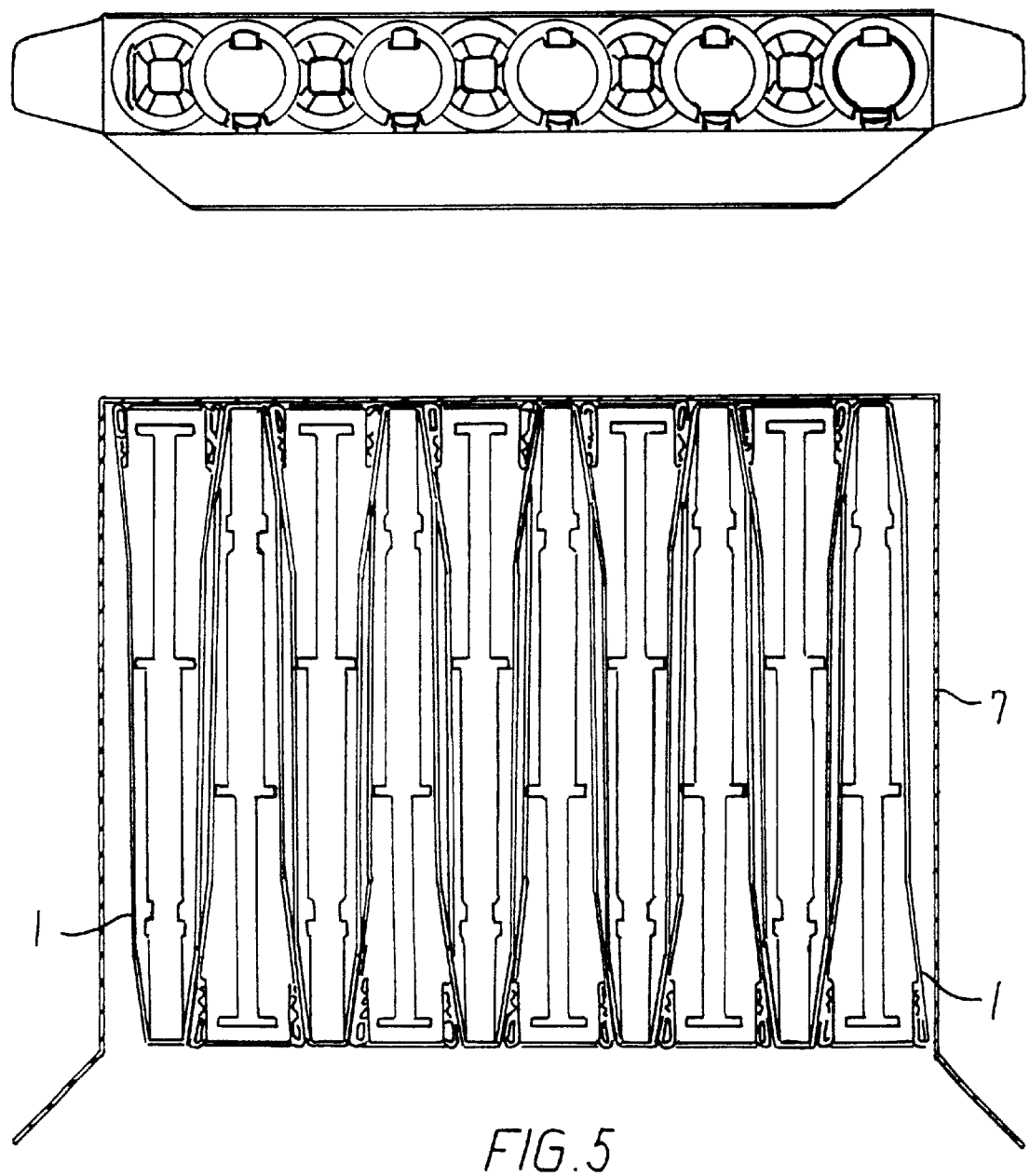
FIG. 5 shows a package with the container with hypodermic syringe partly in section.

FIG. 5 shows a plurality of containers 1 juxtaposed in a package 7. When the container 1 is suitably shaped, stacking possibility before the hypodermic syringe 3 is placed in the container 1 and the plug 5 is applied as well as a small packing volume in the package 7 may be achieved.

Figure 6:
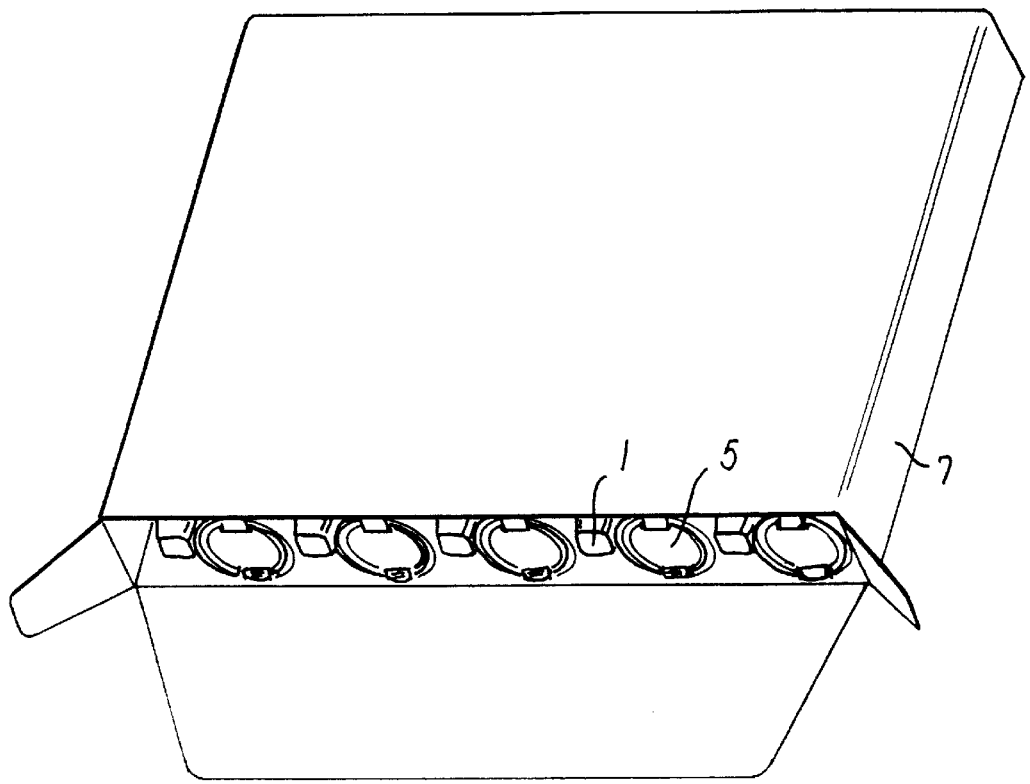
FIG. 6 shows the package in perspective.

FIG. 6 shows a plurality of containers 1 with plugs 5 positioned in a package 7.

In a particular embodiment of the invention in which the container 1 with plug 5 is used for storing the hypodermic needle 3 when this is not in use, the plug 5 is constructed in the manner described below with reference to FIG. 8.

Figure 8:
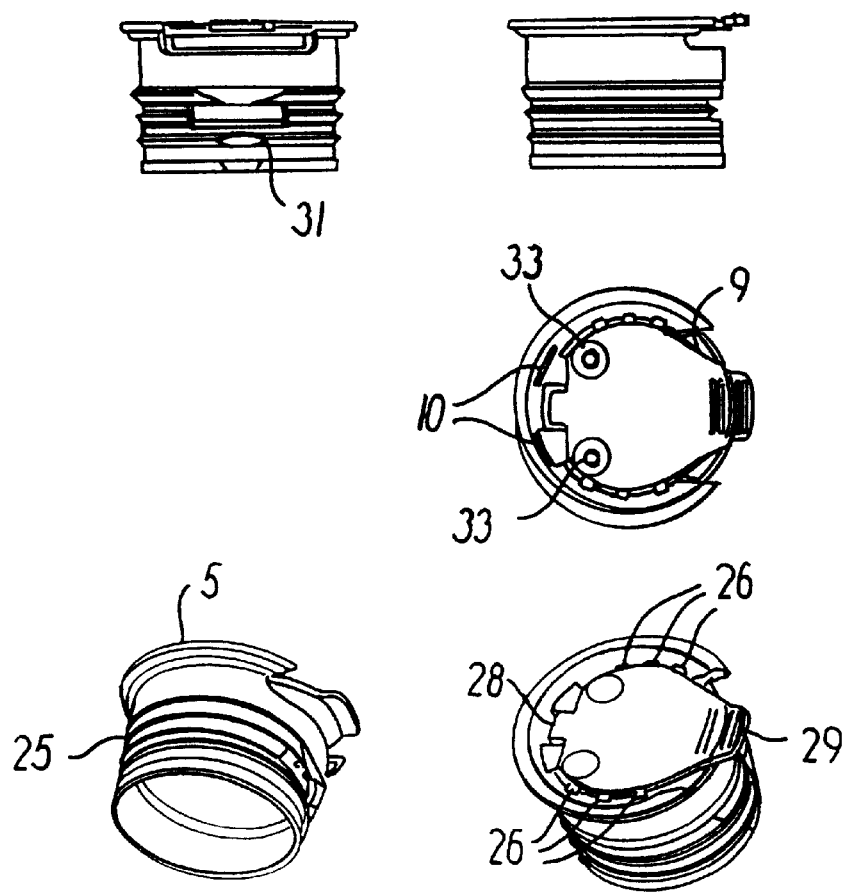
FIG. 8 shows another embodiment of the plug.

In FIG. 8, the plug 5 is provided with two hinges 10 for the connection between the lid 9 and the part of the plug 5 which forms the engagement with the container 1. This part of the plug 5 is called the plug body 25 below. When the plug body 25 and the lid 9 are connected with more than one hinge (see FIG. 8) constructed as a film hinge, it is ensured that the lid 9 is controlled better, so that it is more difficult to work open when the hypodermic syringe has been used and again been arranged in the container 1. In this embodiment, the number of film connections 16 which are broken when the lid 9 is opened, is six, arranged such that there are three on each side of the film hinges 10. In the embodiment shown, both film hinges 10 and film connections 26 are discrete, which means that they are separated from each other so that their mutual position and number may be determined. However, the number and position are not as essential as the function, it being important that the lid may be controlled, and that it is clear to the user whether the container 1 has been opened before. A boss 28 is provided between the hinges 10 shown in this embodiment, said boss 28 being capable of cooperating with the plug body 25 in a radial direction when the lid 9, after completed use of the hypodermic syringe, is pressed down in the plug body 25. Moreover, a second boss 29 or projection is provided in a diametrical position with respect to the previously mentioned boss 28, said second boss 29 serving as a finger grip when the lid 9 is opened. This finger grip cooperates with a groove 31 in the plug body 25 when the lid 9 is pressed down in the body 25 after use. When the finger grip cooperates with the groove 31, the lid 9 is locked, thereby making it difficult to re-open the container 1. The number and the position of radially positioned bosses 28, projections 29 and finger grip are not more essential than their function.

Two knobs 33 are arranged on the lid 9 in an axial direction near the hinges 10. These knobs 33 are to make re-opening of the lid 9 additionally difficult. The number and position of the knobs 33 are likewise less essential as long as the function is achieved.

The lid 9 itself is not necessarily round or circular. It may be oval or elliptic so that the hole in the plug is filled as best as possible when the lid 9 is pressed down in the plug after use. It is almost oval in FIG. 8. The underside of the lid may be provided with various ribs or grooves which can inter alia contribute to controlling the hypodermic syringe when it is in the container.

Figure 7:
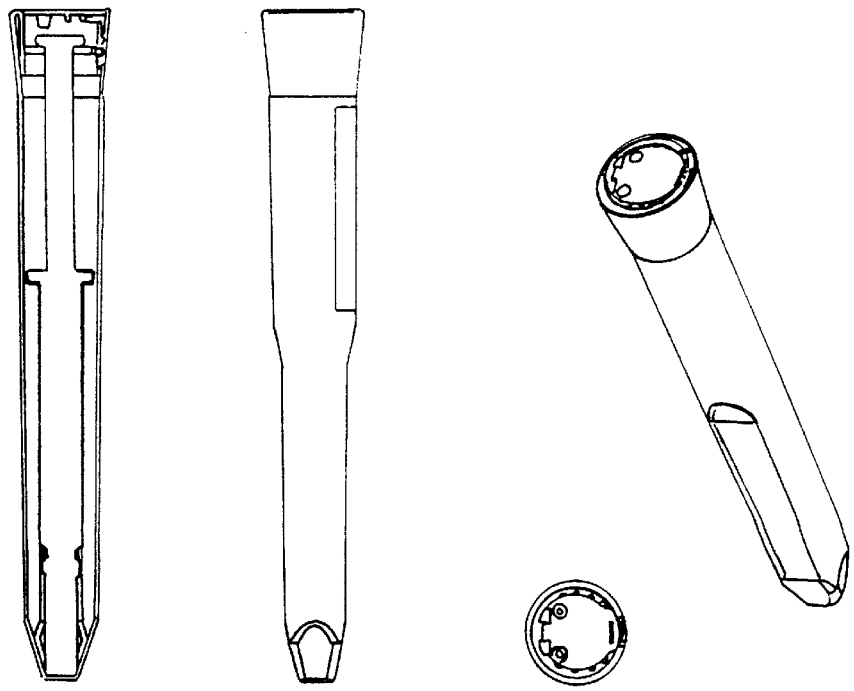
FIG. 7 shows another embodiment of the container.

The container itself may be formed with a writing field 37 (see FIG. 7) which has been obtained by spark machining or sand blasting in the mould. Notes on the individual treatment may be written in this writing field 37.

Figure 9:
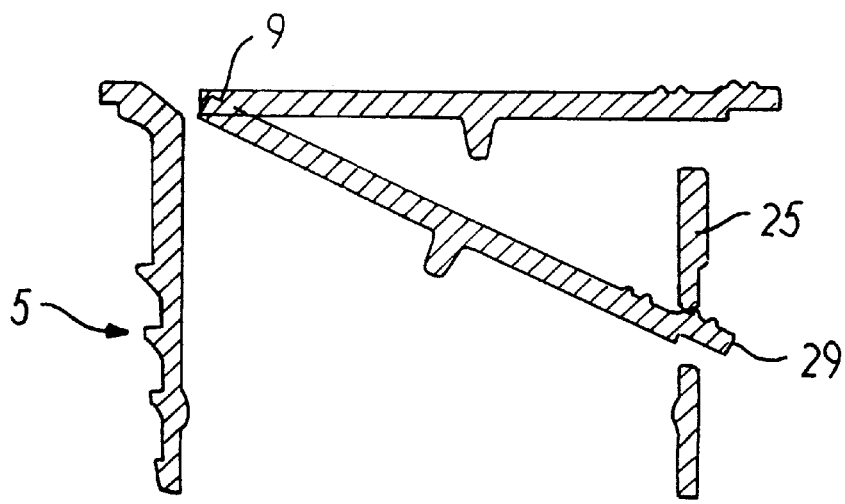
FIG. 9 shows the plug in section, with the lid pressed

FIG. 9 shows a plug 5 in section. The lid 9 is shown in two positions, one before use of the hypodermic syringe, the other after use of the hypodermic syringe. After use of the hypodermic syringe, it is placed in the container and the lid 9 is pressed down in the plug body 25 so that flaps 16 or 29 engage the body 25.

The invention is not restricted to the above-mentioned embodiments, but may be modified by a skilled person in many ways within the scope of the claims. Thus, the hypodermic syringe should be adapted to the container if it is desired to achieve the greatest amount of safety. The selection of material is not critical, as long as the functional requirements are satisfied. It is thus expedient to use ethylene for the plug, since this gives some good breaking properties. On the other hand, it is expedient to use polypropylene for the container, as this gives a solid, dimensionally stable container which may be made almost transparent by injection moulding. There may be one or more flaps, and the film connection may be divided into segments. The injection liquid need not be a liquid proper, it must merely be in a form that may be passed from a hypodermic syringe through a needle-like device into a body. The injection liquid may thus be a powder.

What is claimed is:

1. A container for a hypodermic syringe (3), said container comprising an elongated container body (1) with an opening, and a plug (5) arranged in said opening, wherein the plug (5) comprises a plug body (25) having a through-passage and a lid (9) connected by a hinge (10, characterized in that said hinge is adapted to permit pivotal movement of said lid (9) with respect to said plug body (25) about an axis extending perpendicularly to said through-passage between a first and a second position in which the lid (9) covers at least a part of said opening, and a third position allowing access to said container, said plug body (25) and lid (9) being interconnected by a full or divided film connection (6) defining in an unbroken state said first position, said plug body (25) and said lid (9) being formed with complementary locking means (16, 17, 29, 31) adapted to engage each other in said second position in such a manner that a ready further pivotal movement is not allowed, said film connection (6) and said complementary locking means (16, 17, 29, 31) thereby constituting tamper-proof mechanisms.

2. A container according to the preceeding claim, characterized in that said hinge (10) is formed by at least one film hinge (10).

3. A container according to claim 1, characterized in that said complementary locking means (16, 17, 29, 31) define a snap lock.

4. A container according to the preceeding claim, characterized in that said snap lock comprises a projection (16, 29) arranged on said lid portion (9) and a groove (17, 31) arranged on said plug body (25).

5. A container according to claim 3, characterized in that the plug (5) is formed such that engagement of said complementary locking means (16, 17, 29, 31) requires a pivotal movement of said lid (9) with respect to said plug body (25) from said third position to said second position through said first position.

6. A plug for a closing off the opening of a container body (1) for a hypodermic syringe (3), said plug (5) comprising a plug body (25) connected to a lid (9) by a hinge (10), said plug body (25) being formed by an annular wall defining a through-passage, characterized in that said hinge is adapted to permit pivotal movement of said lid (9) with respect to said plug body (25) about an axis perpendicularly to said through-passage between a first and a second position in which the lid (9) extends across a substantial part of said passage, and a third position in which said passage is not covered, said plug body (25) and said lid (9) being interconnected by a full or divided film connection (6) defining in an unbroken state said first position, and in that said plug body (25) and said lid (9) being formed with complementary snap locking means adapted to engage each other in said second position in such a manner that a ready further pivotal movement is not allowed said film connection (6) and said complementary snap locking means (16, 17, 29, 31) thereby constituting tamper-proof mechanisms.

7. A container according to claim 6, characterized in that said hinge (10) is formed by at least one film hinge (10).

8. A container according to claim 6, characterized in that said complementary snap locking means comprise a projection (16, 29) arranged on said lid (9) and a groove (17, 31) arranged on said plug body (25), and in that engagement of said complementary locking means (16, 17, 28, 29) requires a pivotal movement of said lid (9) with respect to said plug body (25) from said third position to said second position through said first position.

* * * * *